(12) United States Patent
Maki et al.

(10) Patent No.: US 7,280,859 B2
(45) Date of Patent: Oct. 9, 2007

(54) BIOLOGICAL MEASUREMENT PROBE, BIOLOGICAL OPTICAL MEASUREMENT INSTRUMENT USING THE SAME, AND BRAIN FUNCTION MEASUREMENT INSTRUMENT

(75) Inventors: Atsushi Maki, Fuchu (JP); Michiyuki Fujiwara, Kashiwa (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 631 days.

(21) Appl. No.: 10/484,258

(22) PCT Filed: May 24, 2002

(86) PCT No.: PCT/JP02/05078

§ 371 (c)(1),
(2), (4) Date: Jan. 20, 2004

(87) PCT Pub. No.: WO03/041590

PCT Pub. Date: May 22, 2003

(65) Prior Publication Data

US 2004/0236226 A1 Nov. 25, 2004

(30) Foreign Application Priority Data

Nov. 12, 2001 (JP) ............................. 2001-345692

(51) Int. Cl.
*A61B 5/00* (2006.01)

(52) U.S. Cl. ...................................... 600/344; 600/340

(58) Field of Classification Search ................ 600/310, 600/344, 544, 340
See application file for complete search history.

(56) References Cited

U.S. PATENT DOCUMENTS 5,119,815 A * 6/1992 Chance ........................ 600/433
7,039,454 B1 * 5/2006 Kaga et al. .................. 600/476

FOREIGN PATENT DOCUMENTS

WO      WO00/57793      10/2000

* cited by examiner

*Primary Examiner*—Eric F Winakur
(74) *Attorney, Agent, or Firm*—Antonelli, Terry, Stout & Kraus, LLP.

(57) ABSTRACT

The present invention provides a biological measurement probe readily wearable on a biological surface having a large curvature and a measurement technique of simultaneously measuring the blood circulation dynamic change accompanying the auditory/language/visual function activities of a subject (especially baby) and brain waves. A biological measurement probe having illuminating means for illuminating a subject through a first optical waveguide and light collecting means for collecting light illuminated from the illuminating means and propagated through the subject through a second optical waveguide, has first and second guide members having passages through which the first and second optical waveguides are passed and fixing the first and second optical waveguides, and a base member connecting the first guide member to the second one, holding them, and forming a portion brought into contact with the subject.

8 Claims, 10 Drawing Sheets

BIOLOGICAL MEASUREMENT PROBE, BIOLOGICAL OPTICAL MEASUREMENT INSTRUMENT USING THE SAME, AND BRAIN FUNCTION MEASUREMENT INSTRUMENT

TECHNICAL FIELD

The present invention relates to a biological measurement technique of measuring the physiological change in biological tissue.

BACKGROUND ART

As a method for measuring the brain function of a baby, there is disclosed a method for measuring brain waves generated from the brain stem in response to stimulation sounds. This method can mainly measure the response of the brain stem and is difficult to measure the high-order functions controlled by the cerebral cortex.

As a method with light, a method for measuring the activities of the cerebral cortex is proposed. In biological measurement with light, an instrument measuring the biological functions with visible to near infrared light is disclosed in Japanese Patent Application Laid-Open No. 57-115232 or Japanese Patent Application Laid-Open No. 63-275323. Further, a proposal about a brain function image measurement technique by application of this measurement principle (optical topography) is disclosed in Japanese Patent Application Laid-Open No. 9-98972.

These use light guide means, typically, an optical fiber, illuminate biological tissue, and collect and measure the light scattered in biological tissue in the positions several mm to several cm away (hereinafter, abbreviated as the scattering light in biological tissue). Based on the intensity of the measured scattering light in biological tissue, the concentration of absorber in biological tissue, typically, oxygenated Hemoglobin and deoxygenated Hemoglobin, or a value corresponding to the concentration, is obtained. When obtaining the concentration of absorber or the value corresponding to the concentration, the absorption characteristic of targeted absorber corresponding to the wavelength of the illuminating light is used. Typically, when measuring a biological deep part, light which has a wavelength within the range of 650 to 1300 nm and is high in biological permeability, is used.

Such method with light is typically used for biological measurement of a human, in particular, an adult.

The method with light can also measure a baby in view of safety and may measure the high-order brain functions of the baby.

It has been, however, difficult to simultaneously measure the brain stem and the high-order functions accompanying the activities of the cerebral cortex of a baby. If this problem is solved, the low-order to high-order brain functional disorders will be able to be found at an early stage in babyhood. The low-order to high-order brain functional disorders (for example, auditory, language and visual disorders) are often found at the age of two or three and starting speaking. In such case, language acquisition is delayed than normal, thereby requiring tremendous labor for recovering the delay.

A social demand is significant in development of a technical method or an instrument capable of measuring the main brain functional disorders (of the visual, auditory and language functions) at an early stage.

For that purpose, the following two major technical problems (1) and (2) must be solved.

(1) A method for fixing an optical fiber used for the measurement of biological tissue with light The measurement of biological tissue with light has means for illumination with light (hereinafter, abbreviated as illuminating means) and means for collecting light transmitted through biological tissue (hereinafter, abbreviated as light collecting means). As the illuminating means and the light collecting means, an optical waveguide, typically, an optical fiber or an optical fiber bundle, is often used. A set of optical waveguides for illumination and light collection is a minimum unit indicating one measurement position (hereinafter, abbreviated as an illumination and light collection pair).

An instrument performing biological image measurement by setting a plurality of the minimum units is proposed in Japanese Patent Application Laid-Open No. 9-98972. The distance between the illumination position and the light collection position of the illumination and light collection pair (hereinafter, abbreviated as the distance between the illumination and light collection pair) is changed by the size or depth of an area to be measured. The proposal of Japanese Patent Application Laid-Open No. 9-98972 discloses an arrangement form in which an optical waveguide for illumination and an optical waveguide for light collection are arranged alternately on the tops of a square grid so that the distances between the illumination and light collection pairs are equally spaced. Using the arrangement form, one optical waveguide is shared among a plurality of illumination and light collection pairs so as to make image measurement by a small number of optical waveguides. The optical waveguides can be worn on biological tissue in a short time.

The arrangement form can be easily applied to a small area of biological tissue so as to be approximated on the plane of the biological tissue (for example, about 15 cm square for the head), but is difficult to apply to an area having a large curvature. In particular, the head shape of a newborn or a baby has a large curvature so that the difference among individuals is large. When measuring a newborn or a baby, it is impossible for the subject to wait quietly. There arises the problem that the deviation of a probe due to movement must be suppressed, which cannot be expected in an adult.

Means for measuring the brain functions of a newborn or a baby has been limited to an electroencephalogram. The spatial resolution of the electroencephalogram is not very high, making it difficult to separate information on the brain stem as the center part of the brain and the cerebral cortex of the brain surface. On the contrary, a brain function measurement method based on the measurement with light enables non-invasive measurement of the cerebral cortex related strongly to the high-order brain functions particularly developed in a human. It is expected as a very effective method for recognizing the development process of the high-order functions. Although it is known to be effective in principle, a biological measurement probe fixing waveguides for illumination and light collection has not been developed.

DISCLOSURE OF THE INVENTION

To construct a practical biological measurement probe for a newborn or a baby, the following points are required and will be listed below.

a) The character of flexibility:

A biological measurement probe to be used must be flexibly suitable to a biological surface having a curvature b) Holding ability of the distance between waveguides for incidence detection:

In a biological measurement probe to be used, the distance between waveguides for incidence detection (to be exact, the distance between the edges of waveguides for illumination detection, which will be, for convenience, called the distance between incidence detection) must not be changed over the allowable range to the shape having the difference among individuals so as to secure, together with the a), the character of flexibility but the distance does not change.

c) Body movement follow-up ability:

A biological measurement probe to be used must not be deviated due to movement to some degree.

d) Visibility of contact property:

A biological measurement probe to be used must have high visibility and easily control the contact state so as to check the contact property between an optical waveguide and a biological surface.

e) Comfortableness:

The head of a subject having low adaptability to environmental change, such as a newborn or a baby, must not be covered completely from the viewpoint of temperature change.

f) Pressure dispersibility:

A high pressure must not be applied to one point of a subject having the delicate head, such as a newborn or a baby.

g) Shape holding ability:

To reduce a load given to a subject, a probe must be worn in a short time. It is thus necessary to easily change its shape and to hold its basic shape.

h) Wearability:

From the same reason as the g), means for easily fixing a probe is necessary.

i) Suitability to the shape and size of fixing means:

Fixing means must be suitable to the head shape of a subject.

j) Pressurizing ability of fixing means:

Fixing means must give a suitable pressure.

k) The distance between illumination and light collection positions suitable for the brain function measurement of a baby must be obtained.

(2) Brain function examination instrument for baby

To measure the brain functions of the entire brain of a baby, an examination instrument capable of measuring light and brain waves is necessary. Specific problems about this will be listed below.

a) A bed for examination, which is designed to arrange optical fibers and brain wave electrodes on the entire area of the head, is essential. An ordinary bed is difficult to fix a measurement probe on the back part of the head related to the visual function, which is a problem to be solved.

b) A stimulation (visual and auditory) presentation instrument must be arranged in a safe and efficient position.

The present invention has been made in view of the above points and an object of the present invention is to provide a biological measurement probe readily wearable on a biological surface having a large curvature and a biological measurement technique using the same to enable measurement of the physiological change accompanying the activities of the head of a newborn or a baby, which has been difficult to measure.

To achieve the above object, solving means of the above technical problems (1) and (2) which have been performed in the present invention will be described below.

In (1), in the present invention, the optical waveguide fixing part connecting part for connecting the edges of the optical waveguide for incidence and the optical waveguide for light collection and the contact surface brought into contact with biological tissue are integrally formed by a flexible member having a high friction coefficient. The waveguide support part fixing the optical waveguide is adhered by the member.

A flexible thin film member is buried into the member to secure both the character of flexibility and inextensibility (to secure the character of flexibility but the distance does not change). Further, the optimum distance between illumination and light collection positions so as to experimentally increase the sensitivity of a brain function signal, is obtained.

To realize simultaneous making of the measurement of biological tissue with light and the biological electric measurement, typically, brain waves, fixing parts incorporate waveguides for the measurement of biological tissue with light and an electrode and an electric wire of the biological electric measurement.

In (2), in the present invention, sound, visual and language stimulation is given to a subject, and then, a measurement method with light and a method for measuring brain waves are used to simultaneously measure the presence or absence of brain functional disorders from the brain deep part (the brain stem) to the brain surface (the cerebral cortex) of a baby.

In this case, the back part of the head on a bed for examination is released to support the head in the neck and the lower part of the back part of the head. The visual and auditory stimulation instrument is arranged in the safe position in the examination space. The same construction of substantially different sizes can also measure the brain function of an adult.

Representative construction examples of the present invention will be listed below.

A biological measurement probe according to the present invention having illuminating means for illuminating a subject through a first optical waveguide and light collecting means for collecting light illuminated from the illuminating means and propagated through the subject through a second optical waveguide, has first and second guide members having passages through which the first and second optical waveguides are passed and fixing the first and second optical waveguides, and a base member connecting the first guide member to the second one, holding them, and forming a portion brought into contact with the subject. Further, in the construction, the base member is made of a material in which the character of flexibility and biological suitability are high. The biological measurement probe further has extensible members in the first and second guide members for allowing the first and second optical waveguides to be movable in the axial direction.

In the present invention, in the construction, the illuminating means includes a light source for illumination and a light source control circuit controlling an injected current to the light source, and the light collecting means includes an optical detector and a detection signal circuit processing a detection signal obtained by the optical detector.

In the present invention, in the construction, the base member is provided in its inside with an electrode for brain wave measurement together with the first optical waveguide and/or the second optical waveguide so as to simultaneously make the measurement with light and the brain wave measurement.

Further, the present invention provides a biological optical measurement instrument capable of measuring the psychological change in a subject using a biological measurement probe having illuminating means for illuminating the subject through an optical waveguide and light collecting means for collecting light illuminated from the illuminating means and propagated through the subject through an optical waveguide, wherein the probe has first and second guide members having passages through which the optical waveguide for illumination and the optical waveguide for light collection are passed and fixing the optical waveguides, a base member connecting the first guide member to the second one, holding them, and forming a portion brought into contact with the subject, and extensible members in the first and second guide members for allowing the first and second optical waveguides to be movable in the axial direction.

Furthermore, the present invention provides a brain function measurement instrument having a biological optical measurement instrument capable of measuring the psychological change in a subject using a biological measurement probe having illuminating means for illuminating the subject through an optical waveguide and light collecting means for collecting light illuminated from the illuminating means and propagated through the subject through an optical waveguide, a brain wave measurement instrument electrically measuring brain waves, a stimulation controller having data about sound, voice, language and image given to the subject and controlling them, and presenting means for reading data about the sound, voice, language and image and presenting them to the subject, wherein a brain function activity signal of the subject is measured while presenting at least one of the sound, voice, language and image transmitted from the stimulation controller via the presenting means to the subject. The present invention also provides a brain function measurement instrument having the biological measurement probe constructed-such that the base member is provided in its inside with an electrode for brain wave measurement together with the first optical waveguide and/or the second optical waveguide so as to simultaneously make the measurement with light and the brain wave measurement and measuring a brain function activity signal of the subject by the measurement with light and the brain wave measurement.

BRIEF DESCRIPTION OF THE DRAWINGS

FIG. 7(*a*) is a diagram showing the brain wave change of the brain stem of a newborn to simple sounds, which is measured using the instrument shown in FIGS. 4 and 5, and FIGS. 7(*b*) and 7(*c*) are diagrams showing the blood circulation dynamic changes in the brain;

BEST MODE FOR CARRYING OUT THE INVENTION

Embodiments of the present invention will be described below with reference to the drawings.

Using FIG. 1, a wearing example in which optical waveguide fixing parts of biological measurement probes based on the present invention are worn on a subject (here, the head) will be described first.

Figure 1:
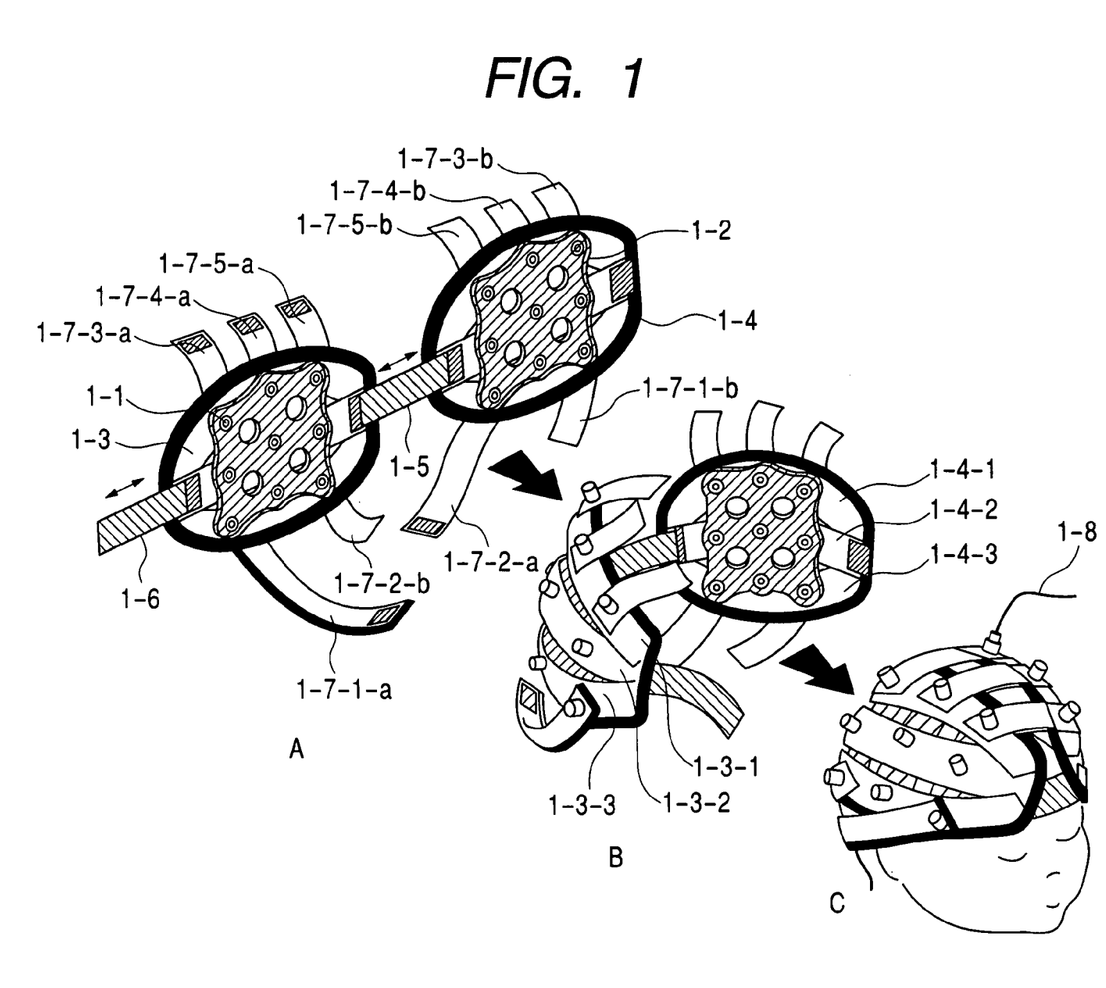
FIG. 1 is a diagram of assistance in explaining a wearing example for wearing biological measurement probes on a subject according to the present invention.

Optical waveguide fixing parts 1-1 and 1-2 shown in FIG. 1 are held by optical waveguide fixing part holding parts 1-3 and 1-4. The optical waveguide fixing part holding parts 1-3 and 1-4 are made of extensible belts or strings 1-3-1, 1-3-2, 1-3-3, 1-4-1, 1-4-2 and 1-4-3, and the extensible belts or strings are connected at both edges of the optical waveguide fixing part holding parts 1-3 and 1-4.

The extensible belts or strings may be light in weight and be as thin as possible so as to easily check the contact state of the optical waveguides. The present invention uses extensible cloth. Different materials having the same function may be used.

Optical-waveguide fixing part holding part connecting parts 1-5 and 1-6 are made for connecting the optical waveguide fixing part holding parts 1-3 and 1-4. The shape and function of the optical waveguide fixing part holding part connecting parts 1-5 and 1-6 are decided by the following reasons.

First, the size of biological tissue is to be measured has the difference among individuals. The connection distance must be changed so as to cope with the difference among individuals. In the present invention, detachable cloth tapes are attached to both edges of the optical waveguide fixing part holding parts 1-3 and 1-4 and both edges of the optical waveguide fixing part holding part connecting parts 1-5 and 1-6, enabling distance adjustment according to the circumferential length of the head.

Second, since the optical waveguide fixing part holding part connecting parts 1-5 and 1-6 are directly brought into contact with the skin of the subject, the width and the subject contact surface must be considered. To avoid the concentration of pressure to the skin of the subject, they may not be thin like the extensible belts or strings forming the optical waveguide fixing part holding parts 1-3 and 1-4 and must have a width to some extent. The width is desirably between 1 and 4 cm. The contact surfaces of the optical waveguide fixing part holding part connecting parts 1-5 and 1-6 with the subject are desirably of a soft material and have a high friction coefficient (to prevent slipping). As the material for that, silicone rubber, sponge, rubber and other organic materials may be used. Needless to say, other materials having an equal function may be used.

When the optical waveguide fixing parts 1-1 and 1-2 are small, wearing by the above-described components is possible. When the optical waveguide fixing parts 1-1 and 1-2 are large, auxiliary holding parts described below must be used to give a uniform pressure to the optical waveguides.

In the present invention, auxiliary holding parts 1-7-1-a to 1-7-5-a and 1-7-1-b to 1-7-5-b are attached. Removable cloth tapes are attached to the edges of the auxiliary holding parts 1-7-1-a to 1-7-5-a and 1-7-1-b to 1-7-5-b. The auxiliary holding parts 1-7-1-a and 1-7-1-b are connected by adjusting the length according to the shape of the head of the subject. Similarly, other auxiliary holding parts are connected by adjusting the length between a and b. As the materials of the auxiliary holding parts 1-7-1-a to 1-7-5-a and 1-7-1-b to 1-7-5-b, extensible belts or strings which are as thin as possible are used.

As in an optical waveguide 1-8, optical waveguides are passed through all optical waveguide guides. The wearing procedure is done in order of A→B→C for simple wearing.

The features of the optical waveguide fixing part holding part will be listed below.

1) The optical waveguide fixing part holding part can be readily and quickly worn.

2) The optical waveguide fixing part holding part can be suitable to various shapes and sizes of subject measurement portions.

3) The optical waveguide fixing part holding part can give a uniform and suitable pressure to the skin of a subject.

The optical waveguide fixing part holding part has various shapes according to measurement portions. The points forming the optical waveguide fixing part holding part are as follows.

1) The optical waveguide fixing part holding part is divided into a plurality of parts to be connected at wearing. (When measuring the entire brain, four planes of two planes of the side parts of the head, one plane of the front part of the head, and one plane of the back part of the head are measured.)

2) Length adjustment can be made in the connection part.

3) An extensible belt or string is used.

To realize the 1) and 2), a detachable cloth tape is used. To realize the 3), an extensible cloth or rubber is used.

Figure 2:
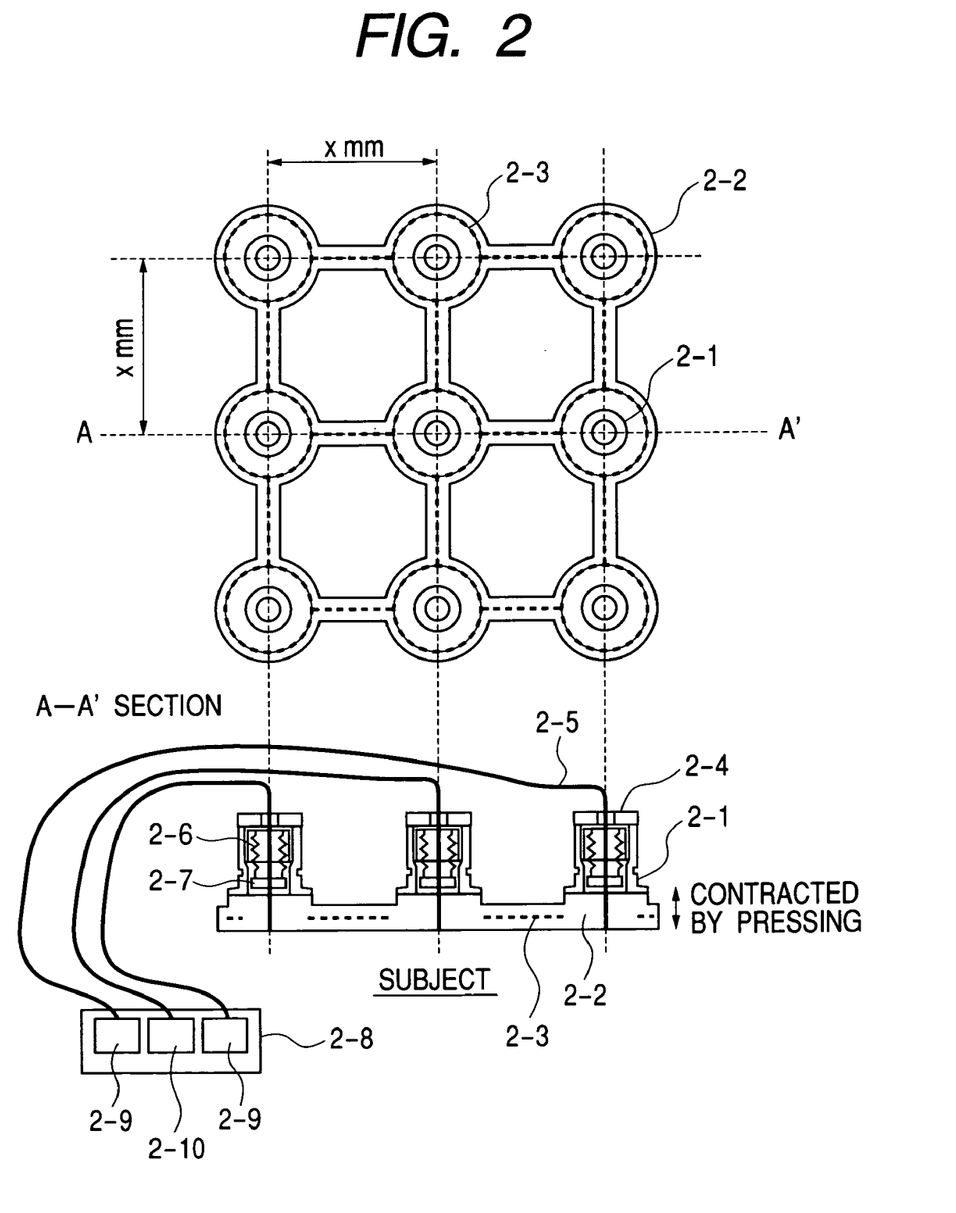
FIG. 2 is a diagram of assistance in explaining a basic construction of an embodiment of the biological measurement probes according to the present invention.

FIG. 2 shows optical waveguide fixing parts in an embodiment of a biological measurement probe of the present invention used for the wearing example shown in FIG. 1. Basically, they are constructed by a repeated pattern. FIG. 2 shows an example of the optical waveguide fixing parts when 9 (=3×3) optical waveguides are fixed. The upper diagram shows only the optical waveguide fixing parts. The A-A' section shown in the lower diagram shows a diagram in which optical waveguides 2-5 and covers 2-4 are worn.

The optical waveguide 2-5 is movable in the vertical direction (along the axial direction of an optical waveguide guide 2-1 in the drawing) by an extensible member 2-6, typically, springs or sponges. The extensible member 2-6 is interposed in an extensible member retainer 2-7 adhered to the cover 2-4 and the optical waveguide 2-5.

The optical waveguide fixing part basically has the optical waveguide guide 2-1, a base 2-2 for connecting and holding the optical waveguide guides, and a thin film or wire 2-3. The optical waveguide guide 2-1 is made of a hard material, typically, plastic. The base 2-2 for connecting and holding the optical waveguide guides is made of a flexible material having high biological suitability, typically, silicone. The thin film or wire 2-3 is made of a plastic material, typically, a PET film. The base 2-2 for connecting and holding the optical waveguide guides is made using a die. It takes a long time for hardening. The optical waveguide guide member 2-1 is arranged during the hardening to fix the base 2-2 for connecting and holding the optical waveguide guides and the optical waveguide guide 2-1. The thin film or wire 2-3 is buried into the base 2-2 for connecting and holding the optical waveguide guides or is adhered to its surface during the hardening.

The optical waveguide fixing part is integrally molded and has the character of flexibility, inextensibility and biological suitability. All the members 2-1 to 2-5 are desirably added black color or a coloring matter absorbing illuminating light or visible light for suppressing the influence of stray light.

In FIG. 2, the end surfaces of the optical waveguides 2-5 brought into contact with a subject are illustrated to be at the same level as the subject contact surface of the base 2-2. In view of the hardness of the base 2-2 and the extensibility of the extensible members 2-6, they are adjusted to be in the positions which give no discomfort feeling to the subject.

The optical waveguides 2-5 are connected to light sources 2-9 and a detector 2-10 in a biological optical measurement instrument 2-8, respectively. In this example, only two light sources and one detector are illustrated. In this embodiment, since the illumination positions and the light collection positions are arranged alternately in the vertical and horizontal directions, there are provided four light sources and five detectors. When the illumination positions and the light collection positions are reversed, there are provided five light sources and five detectors. The illumination positions and the light collection positions are set to 3×3 as a basic construction example. The construction can be easily extended to a pattern of 4×4 or 3×5 or be reduced by erasing of unnecessary portions.

Figure 9:
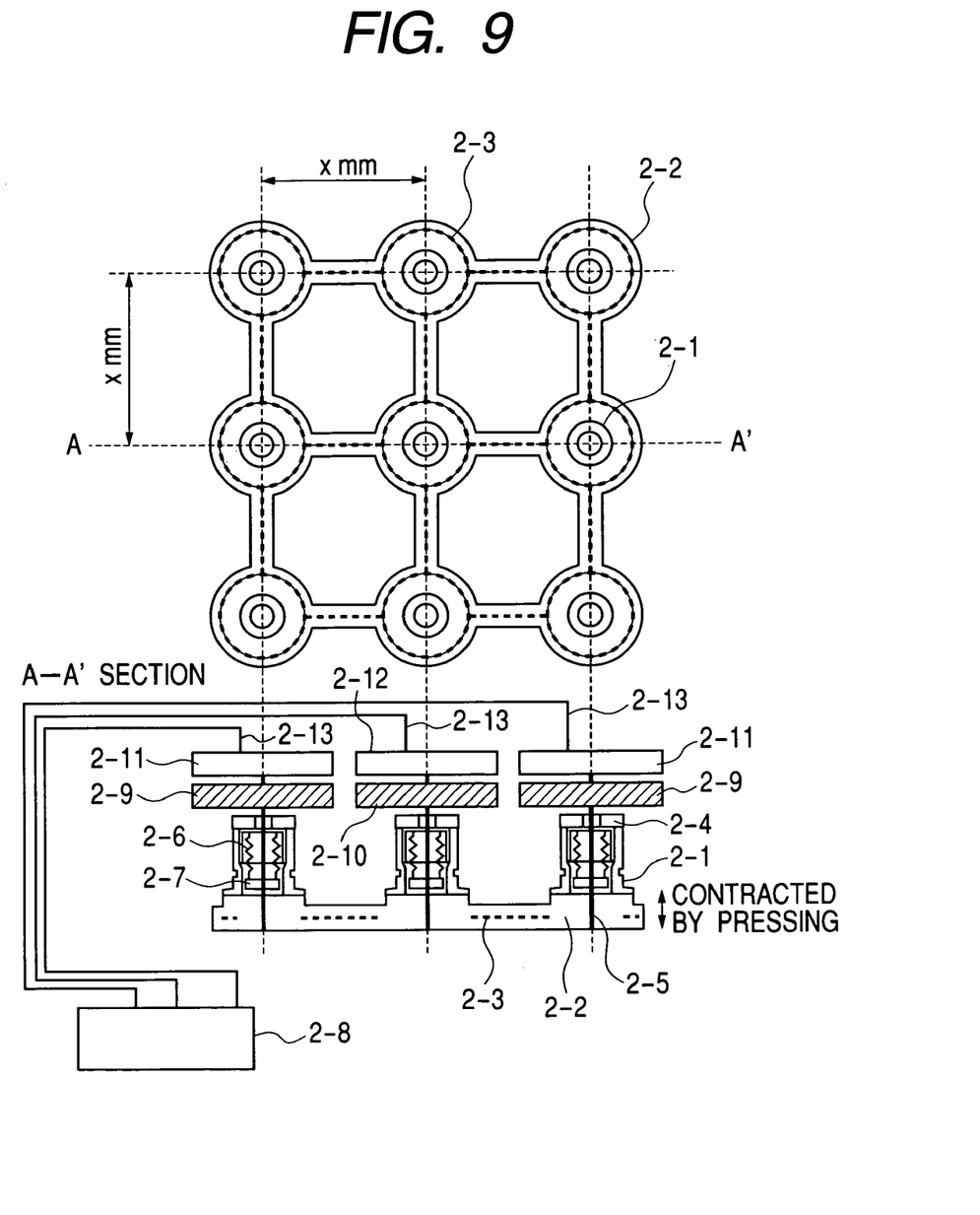
FIG. 9 is a diagram of assistance in explaining another construction example of the biological measurement probes according to the present invention.

FIG. 9 shows another construction example of the biological measurement probes according to the present invention and shows a construction example in which the optical waveguide fixing parts shown in the above-described embodiment include light sources 2-9 necessary for illumination, light source control circuits 2-11 controlling an injected current, a detector 2-10 necessary for optical detection, and a detection signal circuit 2-12 amplifying a detection signal and performing current-voltage conversion.

Depending on the construction of the light source 2-9 and the detector 2-10 can reduce the number of parts by serving as a cover 2-4.

The light source control circuit 2-11 is connected to a biological optical measurement instrument 2-8 for performing mutual communication of necessary information on an injected current and a control signal via a signal and power line 2-13. The detection signal circuit 2-12 is connected to the biological optical measurement instrument 2-8 for performing mutual communication of necessary information on a detection signal and setting of an amplification factor via the signal and power line 2-13. The light source control circuit 2-11, the detection signal circuit 2-12 and the biological optical measurement instrument 2-8 incorporate communication devices to be made wireless by removing any lines other than necessary lines such as power lines.

The optical waveguide 2-5, the light source 2-9 and the detector 2-10 are joined to each other. To attenuate light as noise for a measurement wavelength, such as visible light, a color filter is interposed in the joint parts as necessary.

When applying such construction to the head, the light source detector is arranged directly on biological tissue so that the optical waveguides avoid hair, which provides a significant effect.

Figure 3:
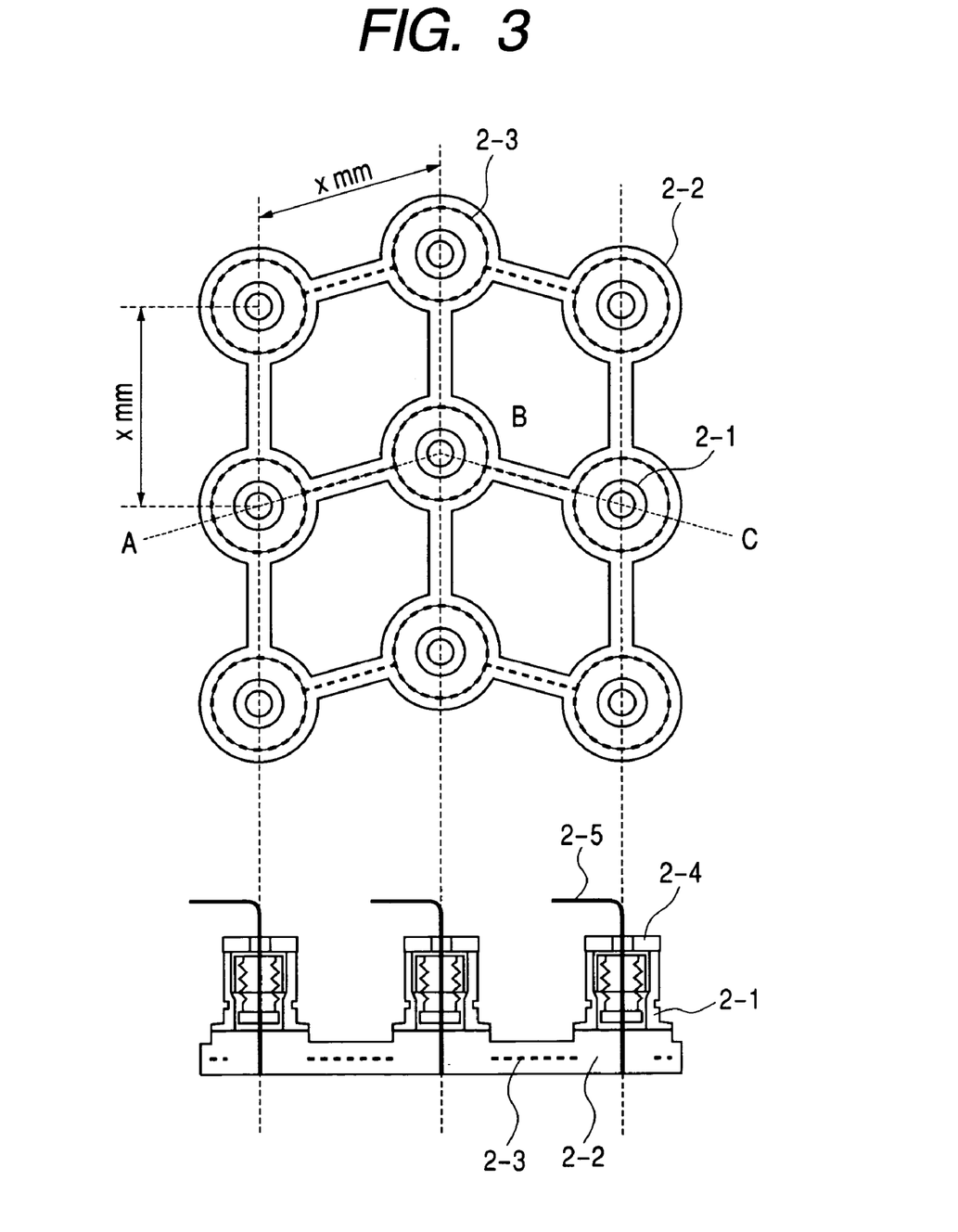
FIG. 3 is a diagram showing a modification pattern of optical waveguide fixing parts shown in FIG. 2.

The base member as shown in FIGS. 2, 3 (described later) and 9 is holed so as not to keep in heat. An electrode for biological electric measurement (such as brain waves) can be provided therein. In consideration of the wearability, the optical waveguide for the measurement of biological tissue with light is desirably integrated with the electrode and wire for the biological electric measurement. When they are integrated with each other, both are generically an energy transmission member, including the signal and power line of the example of FIG. 9.

Figure 10:
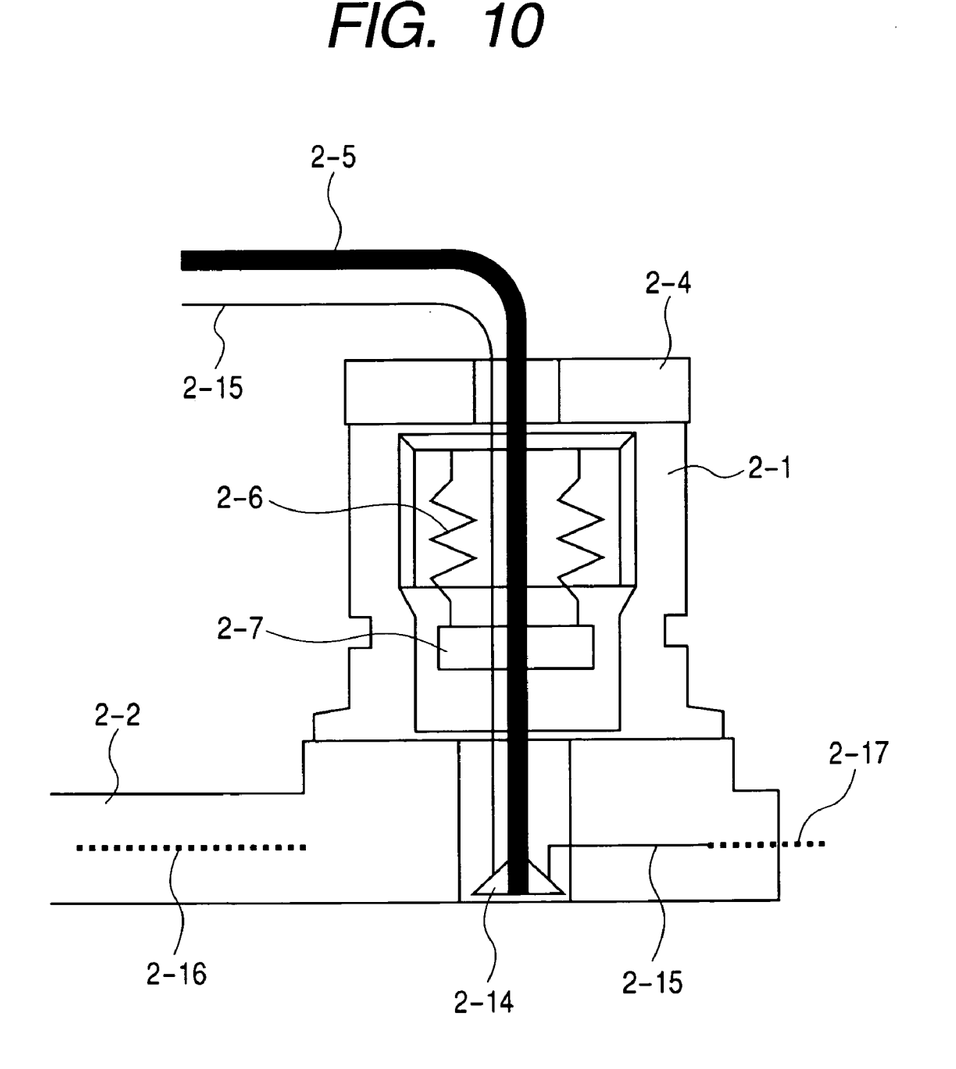
FIG. 10 is a diagram of assistance in explaining a construction example of the biological measurement probe for simultaneously realizing the measurement with light and the brain wave measurement according to the present invention.

FIG. 10 shows a construction example of a biological measurement probe for simultaneously realizing the measurement with light and the brain wave measurement according to the present invention (Only part of FIG. 2 is shown.).

An optical waveguide 2-5 is provided with an electrode 2-14 for brain wave. The middle part of the electrode 2-14 is holed to bring the end surface of the optical waveguide 2-5 into contact with a subject surface. An electric wire 2-15 from the electrode for brain wave to the biological electric measurement instrument is wired along the optical waveguide 2-5 connected to the biological optical measurement instrument. When a thin film or wire 2-3 in a base 2-2 is constructed by an electric wire circuit, a signal from the electrode 2-14 is transmitted by an electric wire or circuit 2-16 in the base 2-2. A plurality of electrodes 2-14 provide an electric wire bundle of the electric wires or circuits 16 which is connected from the base 2-2 via an external electric wire bundle 2-17 to the external biological electric measurement instrument.

As a modification, the electrode 2-14 is not provided in the optical waveguide 2-5 and is provided on the subject on the base 2-2 and the low surface brought into contact with the subject.

The features of the optical waveguide fixing part will be listed below.

1) Since the connecting member is made of a very soft material, the optical waveguide fixing part can be suitable to an arbitrary shape.

2) Since the edges of the optical waveguides are connected to each other, the distance between the optical waveguides is not changed on the subject contact part: This contributes to making the light penetration depth in the measurement portions constant and acquirement of a spatially uniform signal. As shown in FIG. 2, when the distance between the middles of the optical waveguides is 30 mm for manufacture, in the case of being brought into contact with the curved surface in an arbitrary shape, the distance between the edges of the optical waveguides is held 30 mm.

3) Since the connecting member has a suitable friction coefficient, there is no deviation when body movement occurs.

4) Since the unnecessary portion of the connecting part is holed, the visibility for checking the contact property of the optical waveguide is high.

5) There is no wasteful material in the unnecessary portion of the connecting member. Ventilation can be made so that the skin of a subject is not sweaty, which provides high comfortableness.

6) Only the edge of the optical waveguide gives no pressure to the skin surface of a subject and pressure can be given in a large area. Each of the optical waveguide fixing part gives pressure by cushion so that pain to the subject is very little.

Figure 8:
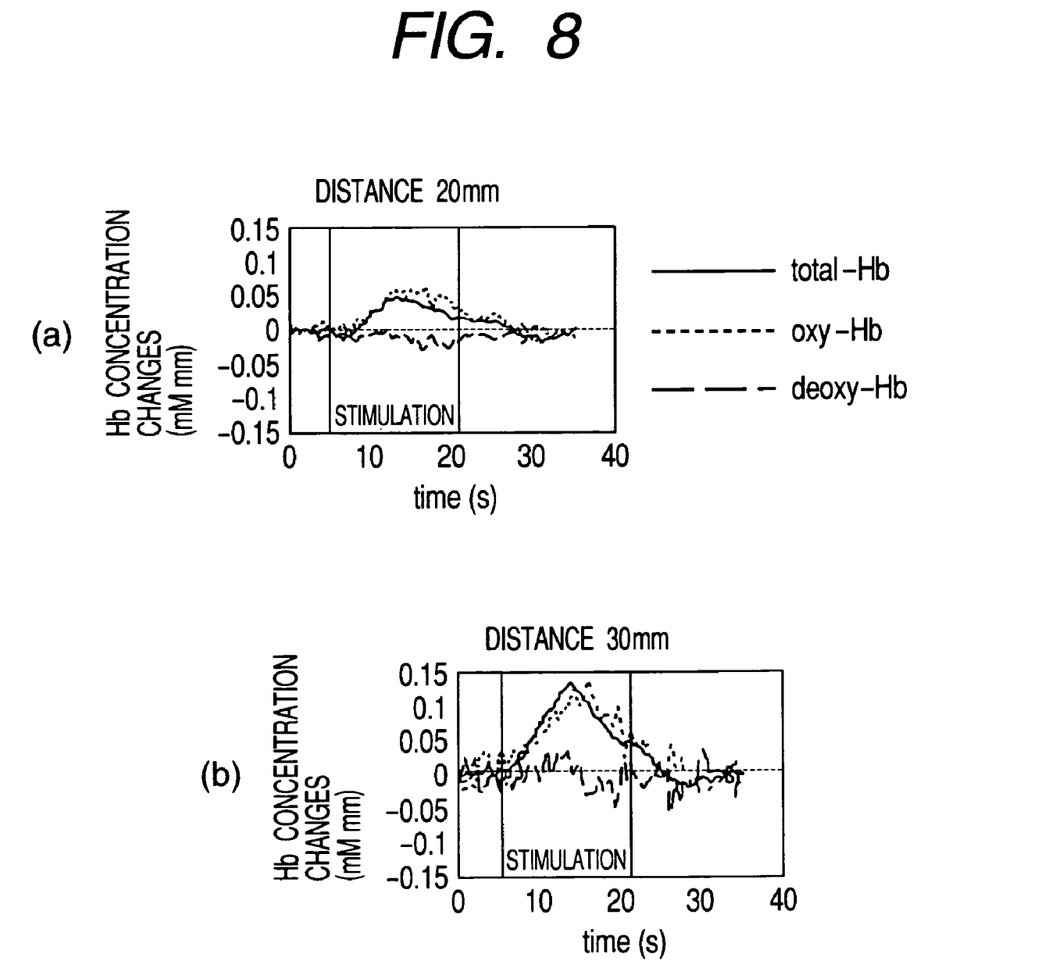
FIG. 8 is a diagram showing the Hemoglobin (Hb) concentration changes in the active brain with time when changing the distance between illumination and light collecting waveguides of the biological measurement probes according to the present invention.

FIG. 8 shows the measured results using the biological measurement probe shown in FIG. 10 and shows the Hemoglobin (Hb) concentration changes in the active brain with time when changing the distance between the illumination and light collection waveguides. The vertical axis indicates the Hb concentration changes and the horizontal axis indicates time. In the drawing, the dotted line indicates the concentration changes of oxygenated Hb (oxy-Hb) carrying oxygen, the dashed line indicates the concentration changes of deoxygenated Hb (deoxy-Hb) in which oxygen is apart, and the solid line indicates values corresponding to the concentration changes of total Hb (total-Hb) as the total of the oxy-Hb concentration changes and the deoxy-Hb concentration changes.

In FIGS. 8(a) and 8(b), measurement is made simultaneously. A baby subject hears conversation in its mother tongue recorded onto a tape during the stimulation period. From this result, the signal of the distance between the illumination and light collection waveguides of 30 mm shown in FIG. 8(b) is larger than that of the distance between the illumination and light collection waveguides of 20 mm shown in FIG. 8(a). It is desirable to set the distance between the illumination and light collection waveguides of 30 mm or more (That is, one side of a grid is 30 mm or more).

FIG. 3 shows a modification pattern of the optical waveguide fixing parts shown in FIG. 2. The square grid pattern shown in FIG. 2 can be used for a biological surface without any disorder. When there is an obstacle on the side part of the head or an ear, it cannot be arranged. In this case, it must be modified to a shape for avoiding the obstacle. In the pattern shown in FIG. 3, the second row is deviated to the upper side (in this case, 1 cm), and an ear can be arranged under the deviated portion. When making such modification, the basic grid shape may be rhombus (including square) so that all the distances between the illumination and light collection positions are constant. The basic construction is the same as FIG. 2 and the description is omitted. The lower diagram shows the A-C section of the upper diagram.

The features of the present invention are advantageous for general use and are not limited to measurement of a baby. While holding the components, the size and the arrangement of the optical waveguides are changed for application to measurement of the head of an adult and in muscles other than the head.

The instrument construction using the biological measurement probes according to the present invention will be described.

Figure 4:
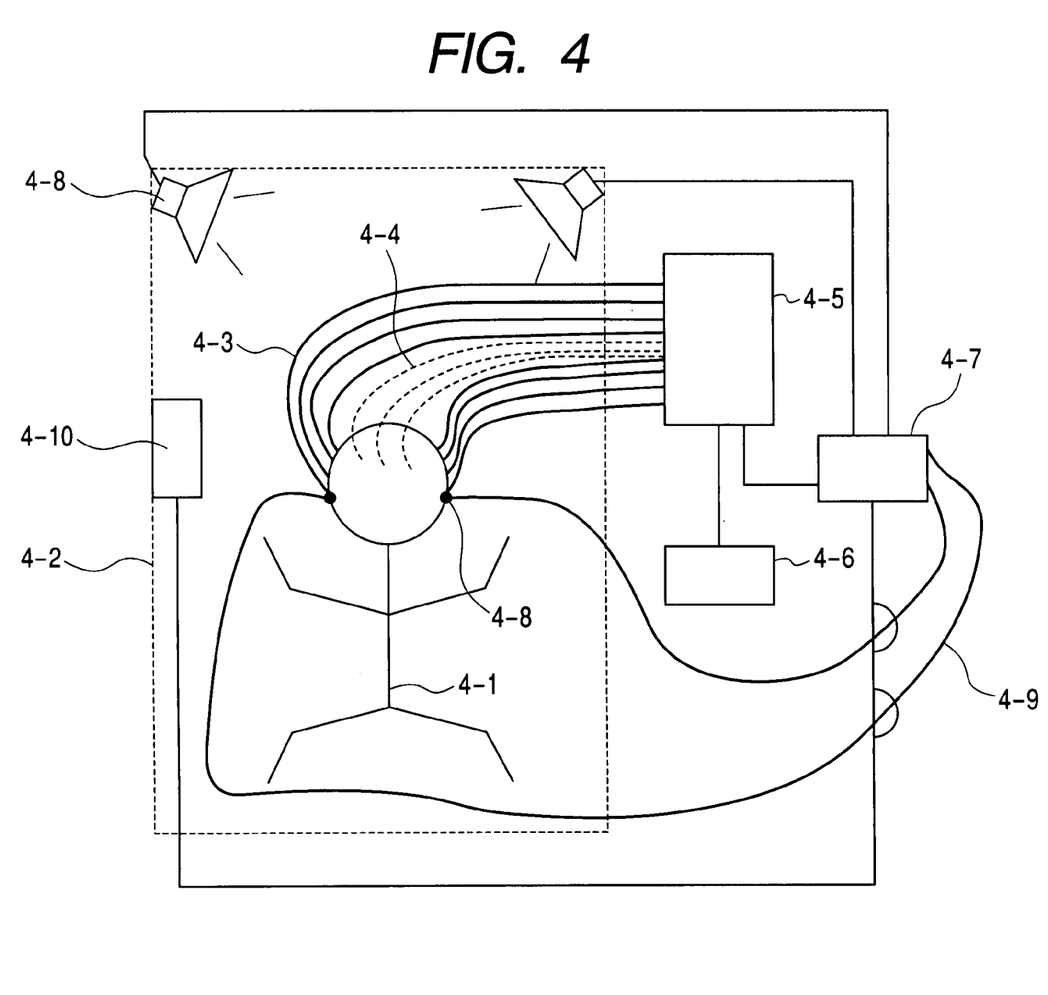
FIG. 4 is a diagram of assistance in explaining an embodiment of a brain function measurement instrument according to the present invention.

FIG. 4 shows an embodiment of a brain function examination instrument based on the present invention. Measurement is made in the state that a subject (for example, a baby) 4-1 lies quietly in a bed or incubator 4-2. A plurality of optical fibers 4-3 (the solid lines) and brain wave electrodes and signal lines 4-4 (the dotted lines) are worn on the head of the baby. The optical fibers include an optical fiber for illumination illuminating the skin of the head with light from the light source thereabove, and an optical fiber for light collection collecting the scattering light transmitted through biological tissue and guiding it to the detector. One area is measured by each combination of them.

Typical illuminating light is near infrared light of near 800 nm having a high biological permeability. From a value of the near infrared light absorbed into the biological tissue, an amount corresponding to the Hemoglobin (Hb) concentration changes (Herein, the concentration refers to an Hb molecule weight in a unit tissue.) can be measured. Hb includes oxy-Hb carrying oxygen and deoxy-Hb in which oxygen is apart. When they are separated for measurement, two suitable wavelengths are selected for measurement. The total-Hb concentration changes as the total of the oxy-Hb concentration changes and the deoxy-Hb concentration changes correspond to the change in blood volume.

It is known that there is a close relation between the brain function activities of an adult, the change in blood volume, the oxy-Hb concentration changes and the deoxy-Hb concentration changes (hereinafter, generically called blood circulation dynamic change). When the activity of the brain function occurs, metabolism is accelerated in the local area in the brain serving as the function to supply oxygen to the area. The blood volume and the oxy-Hb concentration are locally increased to decrease the deoxy-Hb concentration. The change in blood volume, the oxy-Hb concentration changes and the deoxy-Hb concentration changes are measured to recognize the brain function activities of an adult. It has been known that by a method with near infrared light, the brain function activities of an adult can be measured or imaged (see Japanese Patent Laid-Open Application No. Hei 9-98972).

There has not been a method for measuring the blood circulation dynamic change accompanying the brain activities of a newborn or a baby without putting anesthesia. The relation between the brain activities of a baby and the blood circulation dynamic change is unknown. The brain activities themselves are also unknown. In the method with light of this embodiment, the optical fibers 4-1 are only worn on the head. Measurement can be made without putting anesthesia.

Brain waves have already been widely used clinically. The auditory brain stem reaction generated when a sound is heard is effective for finding the auditory disorder at an early stage.

The biological optical measurement instrument mainly measures the cerebral cortex related to the high-order functions. The electroencephalogram measures brain waves generated from the brain stem and the nerve activities of the brain in which the portion cannot be specified relatively. It is difficult to totally decide the brain disorders by either one of them.

In the present invention, a brain function measurement instrument 4-5 integrally incorporates the measurement instrument with near infrared light and the brain wave measurement instrument. They may be separated as necessary. The brain function measurement instrument 4-5 is connected to a plurality of the optical fibers 4-3 and electrodes and signal lines 4-4 and incorporates a plurality of light sources and optical detectors and brain wave potential measurement instruments. The brain function measurement instrument 4-5 performs chronological processing and imaging of the blood circulation dynamic change in biological tissue and brain waves and displays them on a display device 4-6.

An auditory/language/visual stimulation controller 4-7 is an instrument controlling auditory/language/visual stimulation given to a baby. The auditory/language/visual stimulation controller 4-7 writes a plurality of sounds for language/auditory stimulation (beep sounds or click sounds), voices (voices not as languages), languages (voices as languages) and image data (flashing, checker pattern and animation) as analog or digital data. The sound, voice, language and image data are transmitted in arbitrary timing to read and present the sounds, voices and languages by one or more speakers and/or headphones 4-8. An image display device 4-10 displays the image data. The speaker and/or headphone 4-8 and the image display device 4-10 are fixed in the bed or incubator 4-2. Various arrangement positions thereof can be considered. An example will be described later using FIG. 5.

The timing and time in which the sound, voice, language and image data are transmitted from the auditory/language/visual stimulation controller 4-7 and the kinds of the selected sound, voice, language and image data are written into the brain function measurement instrument 4-5. The brain function measurement instrument 4-5 may instruct the timing and the kinds of sound, voice, language and image given as stimulation and the stimulation controller 4-7 may select the written sound, voice and language corresponding to the instruction to output them as signals. It is important that the brain function measurement instrument 4-5 be in synchronization with the auditory/language/visual stimulation controller 4-7 by arbitrary means.

Based on the sound, voice and language from the speaker and/or headphone 4-8 and the image presented on the image display device 4-10, the language/auditory/visual functions are active so that the blood circulation dynamic change occurs in the brain. The blood circulation dynamic change is written into the brain function measurement instrument 4-5. During measurement, the signal is displayed on the display device 4-6. At the completion of all measurements, the processing is performed again and the result is displayed on the display device 4-6. Two or more different signals are displayed on the same screen and the same space-time scale. The user can easily understand the signals.

When the biological measurement probe as shown in FIG. 10 is used, the signal of the measurement with light and the electric measurement signal such as brain wave can be simultaneously measured. The processing results of both signals are displayed on the display device 4-6 by a graph or an image.

Figure 5:
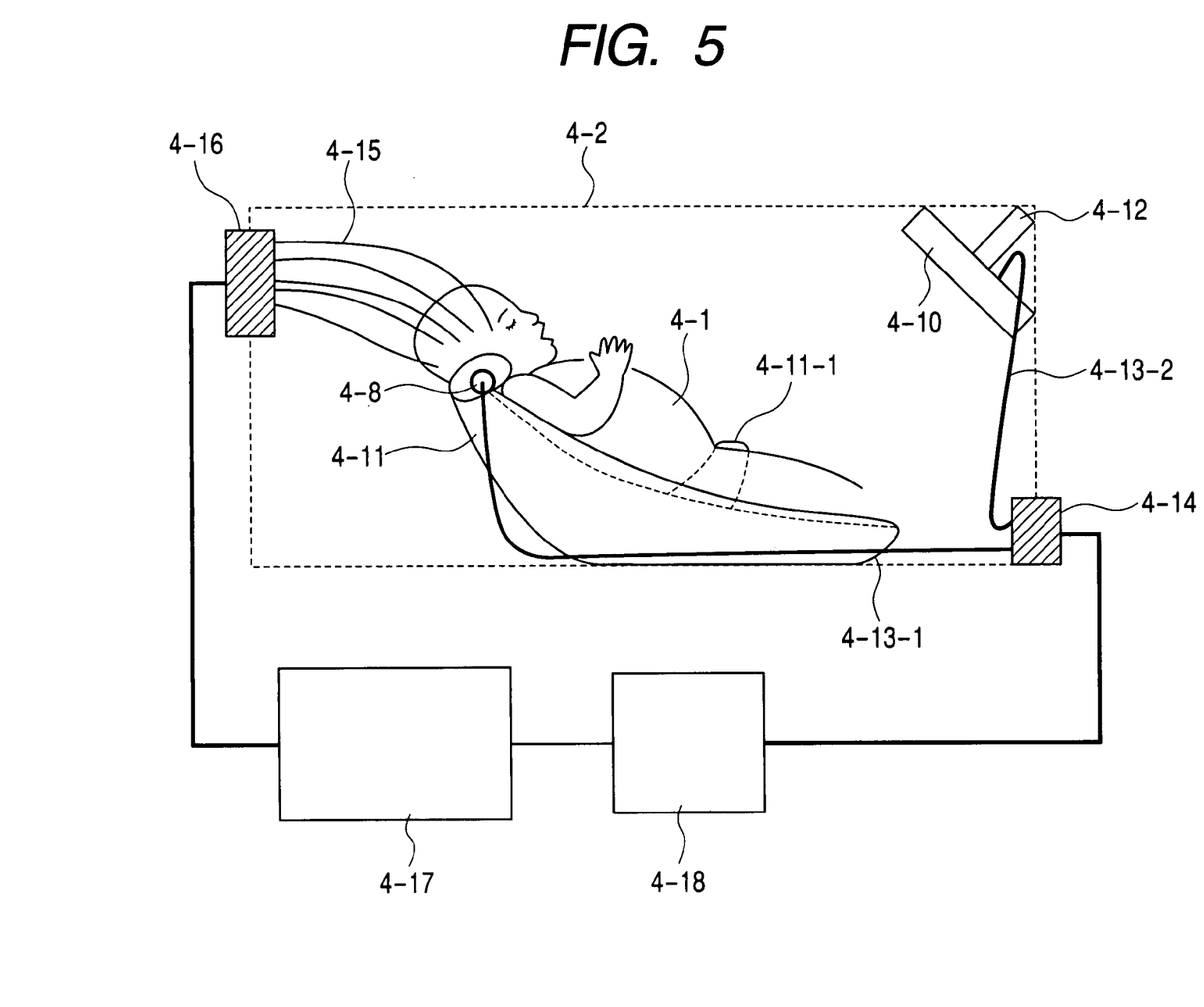
FIG. 5 is a diagram of assistance in explaining a construction example of a subject fixing part in the brain function measurement instrument according to the present invention.

FIG. 5 shows a diagram of a form in which the speaker and/or headphone 4-8 and the image display device 4-10 are arranged in the bed or incubator 4-2, which is viewed from the side.

The bed or incubator 4-2 has a form to surround the subject 4-1, as shown in the drawing, and is made of transparent plastic to be seen from the inside. The subject 4-1 lies quietly on a slant subject fixing part 4-11 to be comfortably measured. A subject legs support part 4-11-1 is fixed onto the subject fixing part 4-11 to be interposed between the legs of the subject 4-1 for preventing the subject 4-1 from being slipped down from the subject fixing part 4-11.

The speakers and/or headphones 4-8 are buried into both sides of the head fixing part of the subject fixing part 4-11. When allowing the subject to hear different sounds simultaneously in the right and left ears, the headphones are more desirable than the speakers.

The image display device 4-10 is fixed onto the position not immediately above the subject 4-1 in the bed or incubator 4-2 using an image display device fixing part 4-12. This arrangement is made in consideration of safety. Even if the image display device 4-10 is dropped, the subject 4-1 will not be injured. Since the subject 4-1 must lie slantly, the slant subject fixing part 4-11 is necessary.

The speaker and/or headphone 4-8 and the image display device 4-10 are connected to a stimulation controller 4-18 (for example, an auditory/language/visual stimulation controller) by signal lines 4-13-1 to 4-13-2. When they are connected via a connector 4-14, they can be easily disconnected. Their positions can be easily changed.

The optical fibers and the brain wave electrodes used for the brain function measurement are connected via a connector 4-16 to a brain function measurement instrument 4-17 by optical fibers and brain wave signal lines 4-15.

Figure 6:
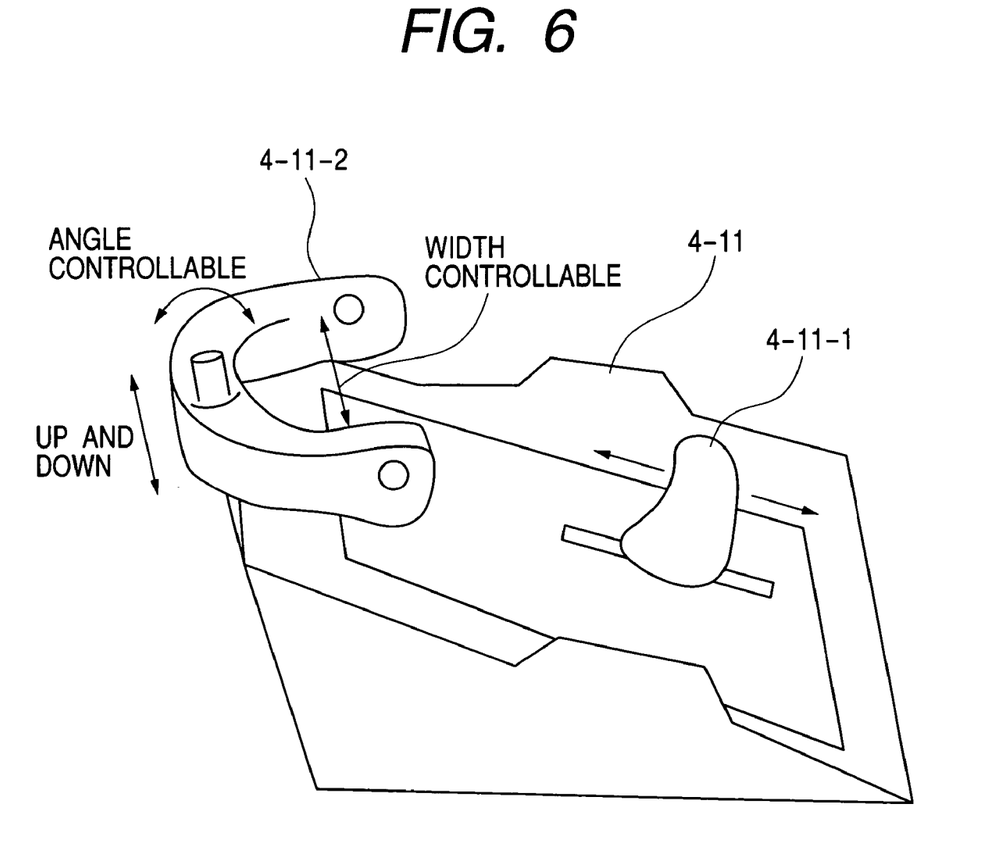
FIG. 6 is a diagram of the subject fixing part shown in FIG. 5 when viewed from slantly above.

FIG. 6 shows a construction example of the subject fixing part 4-11 when viewed from slantly above. The subject legs support part 4-11-1 and a subject head support part 4-11-2 are provided on the subject fixing part 4-11. The subject legs support part 4-11-1 is interposed between the legs of the subject for preventing the subject from being slipped down from the slant subject fixing part 4-11.

The subject head support part 4-11-2 is arranged to support the neck to the lower side of the back part of the head. As shown in the drawing, it is constructed to be width controllable, angle controllable and movable up and down. This shape can release the back part of the head and easily attach the brain function measurement probes. When the subject fixing part is slant, the display device for visual presentation need not be placed immediately above the subject.

Figure 7:
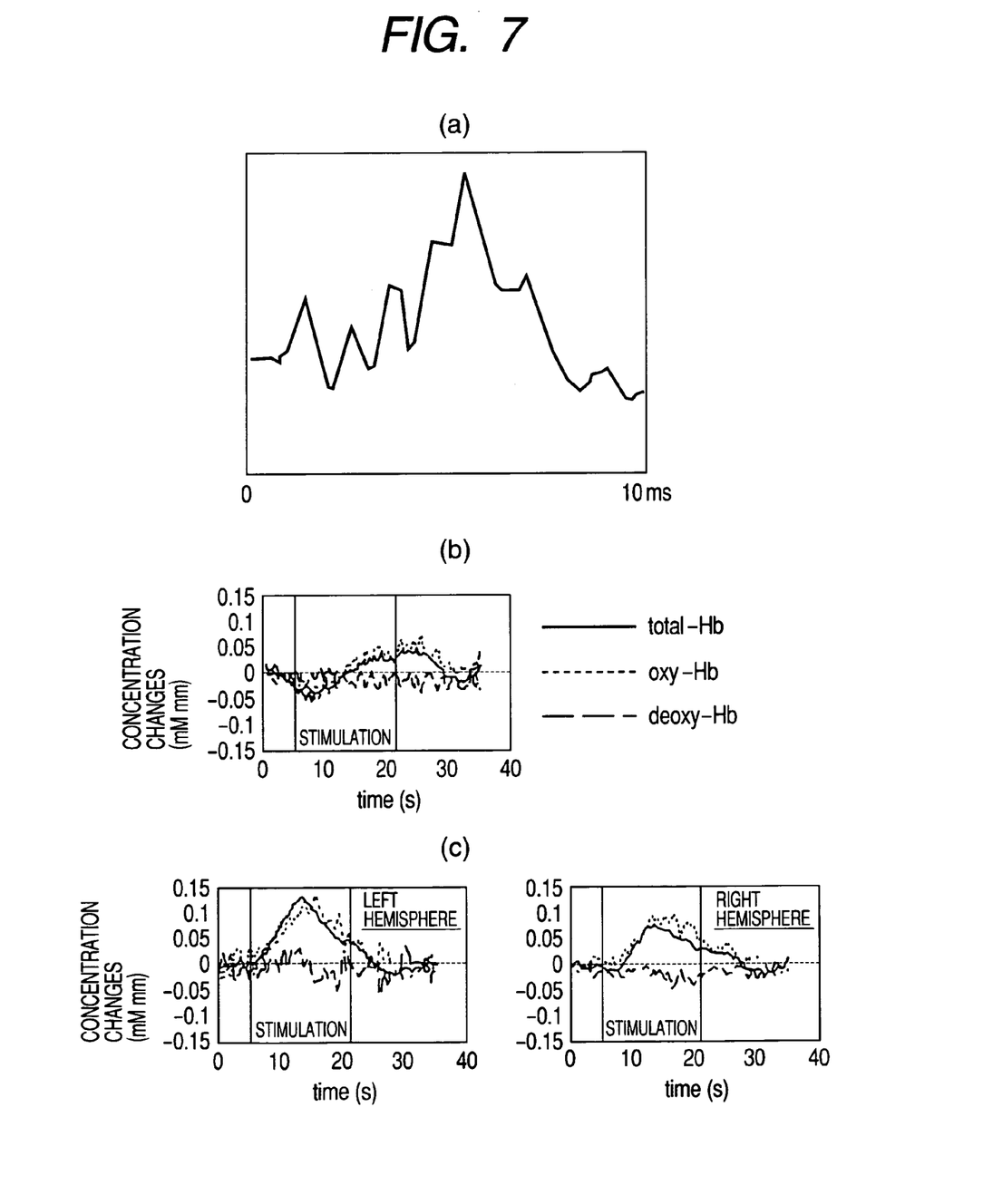

FIG. 7 shows the brain wave change and the blood circulation dynamic changes of a newborn accompanying sounds, which are measured using the instrument shown in FIGS. 4 and 5. FIG. 7(*a*) shows addition average signals of the brain waves of the brain stem to simple sounds when allowing the newborn to hear the simple sounds (click sounds of 200 ms) with repetition of about 1000 times. When the auditory function is not abnormal, the brain waves having 6 to 7 peaks within 10 ms after hearing the sound as the reaction of the brain stem, are observed, as shown in the drawing.

The graphs of FIGS. 7(*b*) and 7(*c*) show the blood circulation dynamic changes in the brain accompanying the reaction of the cerebral cortex with the simple sounds and conversation. The vertical axis of the graphs of FIGS. 7(*b*) and 7(*c*) indicates values corresponding to the total-Hb, oxy-Hb and deoxy-Hb concentration changes. The horizontal axis thereof indicates time. The solid line indicates total Hb, the dotted line indicates oxy-Hb, and the dashed line indicates deoxy-Hb.

The results of FIGS. 7(*b*) and 7(*c*) show data obtained by measuring the position 1.5 cm above from the ear hole on the left side part of the head of the newborn. In FIGS. 7(*b*) and 7(*c*), 35 seconds of a stimulation period of 15 seconds, 5 seconds before the stimulation period and 15 seconds after the stimulation period are extracted as one block for each stimulation. The stimulation is repeated 10 times in FIGS. 7(*b*) and 7(*c*). Ten blocks are addition averaged to obtain chronological data of the blood circulation dynamic change.

Of the results, in FIG. 7(*a*), the auditory signals are transmitted at least from the ears to the brain stem of the subject, indicating normal reaction. The signal transmission from the brain stem to the cerebral cortex is difficult to be specified by the brain waves. It is decided by the result of the measurement with light capable of measuring the reaction of the blood circulation dynamic change accompanying the activity of the cerebral cortex. With the simple sounds, a significant reaction does not occur in the cerebral cortex, as shown in FIG. 7(*b*). The reason is because the cerebral cortex controlling the high-order functions is not very active with the simple sounds. As shown in FIG. 7(*c*), however, when hearing complicated sounds such as language (conversation), the cerebral cortex of the newborn is very active and recognizes the language. From this result, the auditory and language functions of the subject perform normally.

The present invention will be summarized as follows.

1) A biological measurement probe having illuminating means for illuminating a subject through a first optical waveguide and light collecting means for collecting light illuminated from the illuminating means and propagated through the subject through a second optical waveguide, having first and second guide members having passages through which the first and second optical waveguides are passed and fixing the first and second optical waveguides, and a base member connecting the first guide member to the second one, holding them, and forming a portion brought into contact with the subject.

2) The biological measurement probe according to the construction of the 1), wherein the base member is made of a material in which the character of flexibility and biological suitability are high.

3) The biological measurement probe according to the construction of the 1), further having extensible members in the first and second guide members for allowing the first and second optical waveguides to be movable in the axial direction.

4) The biological measurement probe according to the construction of the 1), wherein the first and second guide members are arranged on the base member to be alternate on the top positions of a square grid shape or a rhombus grid shape.

5) The biological measurement probe according to the construction of the 1), wherein the portion of the base member brought into contact with the subject consists of a plurality of divided plane-structure members, and the plane-structure members are connected through flexible members.

6) The biological measurement probe according to the construction of the 1), wherein the illuminating means includes a light source for illumination and a light source control circuit controlling an injected current to the light source, and the light collecting means includes an optical detector and a detection signal circuit processing a detection signal obtained by the optical detector.

7) The biological measurement probe according to the construction of the 1), wherein the base member is provided in its inside with an electrode for brain wave measurement together with the first optical waveguide and/or the second optical waveguide so as to simultaneously make the measurement with light and the brain wave measurement.

8) A biological optical measurement instrument capable of measuring the psychological change in a subject using a biological measurement probe having illuminating means for illuminating the subject through an optical waveguide and light collecting-means for collecting light illuminated from the illuminating means and propagated through the subject through an optical waveguide, wherein the probe has first and second guide members having passages through which the optical waveguide for illumination and the optical waveguide for light collection are passed and fixing the optical waveguides, a base member connecting the first guide member to the second one, holding them, and forming a portion brought into contact with the subject, and extensible members in the first and second guide members for allowing the first and second optical waveguides to be movable in the axial direction.

9) The biological optical measurement instrument according to the construction of the 8), wherein the illuminating means includes a light source for illumination and a light source control circuit controlling an injected current to the light source, the light collecting means includes an optical detector and a detection signal circuit processing a detection signal obtained by the optical detector, and the light source control circuit and the detection signal circuit are controlled via communication means, respectively.

10) A brain function measurement instrument having a biological optical measurement instrument capable of measuring the psychological change in a subject using a biological measurement probe having illuminating means for illuminating the subject through an optical waveguide and light collecting means for collecting light illuminated from the illuminating means and propagated through the subject through an optical waveguide, a brain wave measurement instrument electrically measuring brain waves, a stimulation controller having data about sound, voice, language and image given to the subject and controlling them, and presenting means for reading data about the sound, voice, language and image and presenting them to the subject, wherein a brain function activity signal of the subject is measured while presenting at least one of the sound, voice, language and image transmitted from the stimulation controller via the presenting means to the subject.

11) A brain function measurement instrument, wherein the biological measurement probe according to the 7) is used to measure a brain function activity signal of the subject by the measurement with light and the brain wave measurement.

12) A brain function measurement instrument having a biological optical measurement instrument having illuminating means for illuminating biological tissue and light collecting and detecting means for collecting and detecting light transmitted through the biological tissue, a brain wave measurement instrument measuring brain waves, a sound stimulation controller having a plurality of data about sound, voice and language, a speaker or headphone presenting the sound, voice and language to a baby subject, a visual stimulation controller having a plurality of data about image, and an image display device presenting the image to the subject, wherein a brain function activity signal of the subject is measured while the sound, voice and language from the sound stimulation controller and the image data from the visual stimulation controller are read from the speaker or headphone and the image display device to present them to the subject.

13) The brain function measurement instrument according to the 12), wherein the speaker or headphone and the image display device reading stimulation and presenting it to the subject are integrally provided in a bed or incubator in which the subject lies.

14) The brain function measurement instrument according to the 12), wherein a fixing part fixing the subject in the bed in which the subject lies is slant.

15) The brain function measurement instrument according to the 12), wherein the speaker or headphone is provided in the fixing part fixing the subject in the bed or incubator in which the subject lies.

16) The brain function measurement instrument according to the 12), wherein the image display device is fixed in the position not immediately above the subject in the bed or incubator in which the subject lies.

17) The brain function measurement instrument according to the 12), wherein the fixing part fixing the subject has a member supporting the legs of the subject.

18) The brain function measurement instrument according to the 12), wherein the fixing part fixing the subject in the bed in which the subject lies has members supporting the head and the neck of the subject so as to release the back part of the head.

19) The brain function measurement instrument according to the 12), wherein the fixing part fixing the subject in the bed in which the subject lies is slant, has a member supporting the legs of the subject, and has members supporting the head and the neck of the subject so as to release the back part of the head.

20) The fixing part fixing the subject according to the 17), wherein the member supporting the legs of the subject is movable.

21) The fixing part fixing the subject according to the 18), wherein the members supporting the head and the neck of the subject is movable to change the shape.

22) A brain function measurement instrument having a biological optical measurement instrument having illuminating means for illuminating biological tissue and light collecting and detecting means for collecting and detecting light transmitted through the biological tissue, a brain wave measurement instrument measuring brain waves, a sound stimulation controller having a plurality of data about sound, voice and language, a speaker or headphone presenting the sound, voice and language to a baby subject, a visual stimulation controller having a plurality of data about image, and an image display device presenting the image to the subject, wherein the biological optical measurement instrument, the brain wave measurement instrument, the sound stimulation controller and the visual stimulation controller are in synchronization with each other for transmitting and receiving a signal of timing, time, length and the kinds of stimulation presenting sound, voice, language and image stimulation, reading the sound, voice, language and image data from the sound stimulation controller and the visual stimulation controller in synchronization with the signal from the speaker or headphone and the image display device, and presenting them to the subject.

INDUSTRIAL APPLICABILITY

According to the present invention, the probe for the measurement of biological tissue with light based on the present invention readily wearable on a biological surface having a large curvature can measure the psychological change in the head or the motion portion such as the arm of a newborn or a baby, which has been difficult to measure.

Since the brain functions of a baby including a newborn can be measured, the brain disorders of the baby can be found at an early stage. In particular, the brain wave measurement and the measurement with light are united to simultaneously measure both the brain deep part and the cerebral cortex, realizing total brain function measurement and facilitating decision of the brain functional disorders.

According to the present invention, the application field of the measurement of biological tissue with light is expanded and significantly contributes to the industry. In particular, understanding of the development process of the brain functions contributes to the field exerting a significant influence on the society such as education.

The invention claimed is:

1. A biological measurement probe comprising illuminating means for illuminating the head of a subject through a plurality of optical waveguides and light collecting means for collecting light illuminated from said illuminating means and propagated through the subject through a plurality of other optical waveguides;
   a plurality of optical waveguide fixing parts each having a plurality of optical waveguide fixing members for fixing the plurality of optical waveguides;
   a plurality of holding parts holding and covering the plurality of optical waveguide fixing parts, said plurality of holding parts being constructed with extensible belts or strings, and pressing the plurality of optical waveguides to the head of the subject when the probe is installed on the head of the subject; and
   a plurality of connecting parts connecting respective holding parts.

2. The biological measurement probe according to claim 1, wherein the optical waveguide fixing members are arranged on the optical waveguide fixing parts in such manner that the optical waveguides for illumination and the optical waveguides for collection are alternately disposed on top positions of a square grid shape or a rhombus grid shape.

3. The biological measurement probe according to claim 1, wherein the illuminating means includes a light source for illumination and a light source control circuit controlling an injected current to the light source, and the light collecting means includes an optical detector and a detection signal circuit processing a detection signal obtained by the original detector.

4. The biological measurement probe according to claim 1, wherein the optical waveguide fixing members are each provided with an internally disposed electrode for brain wave measurement together with the optical waveguide so as to simultaneously make the measurement with light and the brain wave measurement.

5. The biological measurement probe according to claim 1, wherein the cross-section area of the optical waveguides at the side contacting to the head of the subject broadens as approaching the end surface of the optical waveguides.

6. A biological optical measurement instrument, comprising:

a biological measurement probe having illuminating means for illuminating the head of a subject through a plurality of optical waveguides and light collecting means for collecting light illuminated from said illuminating means and propagated through the subject through a plurality of other optical waveguides, comprising:

a plurality of optical waveguide fixing parts each having a plurality of optical waveguide fixing members for fixing the plurality of optical waveguides, and a plurality of holding parts holding and covering the plurality of optical waveguide fixing parts, said plurality of holding parts being constructed with extensible belts or strings, and pressing the plurality of optical waveguides to the head of the subject when the probe is installed on the head of the subject, and a plurality of connecting parts connecting respective holding parts, wherein the optical waveguide fixing members are each provided with an internally disposed electrode for brain wave measurement together with the optical waveguide so as to simultaneously make the measurement with light and the brain wave measurement, and stimulation presenting means for presenting a stimulation to the subject.

7. The biological optical measurement instrument according to claim 6, further comprising a bed on which the subject lies down.

8. The biological optical measurement instrument according to claim 7, further comprising a fixing part for fixing the subject in the bed.

* * * * *